(12) United States Patent
Ha

(10) Patent No.: US 11,116,523 B2
(45) Date of Patent: Sep. 14, 2021

(54) FEMORAL TUNNEL GUIDE DEVICE

(71) Applicant: Samsung Life Public Welfare Foundation, Seoul (KR)

(72) Inventor: Chul Won Ha, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 76 days.

(21) Appl. No.: 16/339,826

(22) PCT Filed: Sep. 27, 2017

(86) PCT No.: PCT/KR2017/010694
§ 371 (c)(1),
(2) Date: Apr. 5, 2019

(87) PCT Pub. No.: WO2018/066873
PCT Pub. Date: Apr. 12, 2018

(65) Prior Publication Data
US 2020/0046380 A1    Feb. 13, 2020

(30) Foreign Application Priority Data
Oct. 6, 2016   (KR) .................. 10-2016-0129087

(51) Int. Cl.
*A61B 17/17* (2006.01)
*A61B 17/34* (2006.01)
(Continued)

(52) U.S. Cl.
CPC ...... *A61B 17/1714* (2013.01); *A61B 17/3403* (2013.01); *A61B 17/3468* (2013.01);
(Continued)

(58) Field of Classification Search
CPC . A61B 17/17; A61B 17/1714; A61B 17/1717; A61B 17/1721; A61B 17/1725;
(Continued)

(56) References Cited

U.S. PATENT DOCUMENTS 5,514,144 A * 5/1996 Bolton ............... A61B 17/1714
606/96
5,681,333 A    10/1997 Burkhart et al.
(Continued)

FOREIGN PATENT DOCUMENTS

FR          2744621 A1   8/1997
KR   10-2014-0048301 A   4/2014
(Continued)

OTHER PUBLICATIONS

Extended European Search Report prepared by European Patent Office for corresponding European application 17858667.3 dated Jun. 3, 2020.
(Continued)

*Primary Examiner* — Kevin T Truong
*Assistant Examiner* — Lisa Nguyen
(74) *Attorney, Agent, or Firm* — McCarter & English, LLP

(57) ABSTRACT

Provided is a femoral tunnel guide device including: a handle; a guide tube coupled to the handle and extending in one direction: and an offset unit extending from the guide tube and spaced apart by a predetermined distance from a virtual extension line of the guide tube in the one direction.

5 Claims, 5 Drawing Sheets

(51) Int. Cl.
*A61B 17/56* (2006.01)
*A61F 2/08* (2006.01)

(52) U.S. Cl.
CPC ........ *A61B 17/562* (2013.01); *A61B 17/1764* (2013.01); *A61B 2017/564* (2013.01); *A61F 2/0811* (2013.01)

(58) Field of Classification Search
CPC ............ A61B 17/1764; A61B 17/1778; A61B 17/1796; A61B 17/34; A61B 17/3403
See application file for complete search history.

(56) References Cited

U.S. PATENT DOCUMENTS

| | | | |
|---|---|---|---|
| 5,683,401 A * | 11/1997 | Schmieding | A61B 17/8875 606/104 |
| 7,104,995 B2 * | 9/2006 | Crofford | A61B 17/175 606/81 |
| 2003/0009173 A1 | 1/2003 | McGuire et al. | |
| 2005/0228368 A1 | 10/2005 | Yon et al. | |
| 2005/0228399 A1 | 10/2005 | Kubo et al. | |
| 2007/0191853 A1 | 8/2007 | Stone | |
| 2010/0049200 A1 | 2/2010 | Re | |
| 2013/0184610 A1 * | 7/2013 | Bourque | A61B 17/1675 600/585 |
| 2016/0074151 A1 * | 3/2016 | Pfeiffer | A61F 2/0811 623/13.17 |
| 2017/0080166 A1 * | 3/2017 | Bagwell | A61B 17/3403 |
| 2018/0243048 A1 * | 8/2018 | Shan | A61B 8/4218 |
| 2020/0179056 A1 * | 6/2020 | Ando | A61B 1/00147 |

FOREIGN PATENT DOCUMENTS

| | | |
|---|---|---|
| WO | WO 2011/056279 A1 | 5/2011 |
| WO | WO 2014/179802 A2 | 11/2014 |

OTHER PUBLICATIONS

International Search Report and Written Opinion Issued by the Korean Intellectual Property Office, acting as the ISA, for International Application PCT/KR2017/010694 dated Jan. 12, 2018.

Chung, Jun Young et al.: "Anatomic placement of the femoral tunnel by a modified transtibial technique using a large-offset femoral tunnel guide: A cadaveric study", *The Knee*, 23 (2016), pp. 659-665.

* cited by examiner

FEMORAL TUNNEL GUIDE DEVICE

CROSS-REFERENCE TO RELATED APPLICATIONS

This application is the National. Stage entry under 35 U.S.C. § 371 of International Application Number PCT/K 2017/010694 filed on Sep. 27, 2017, published on Apr. 12, 2018 under publication number WO 2018/066873 A1, which claims the benefit of priority under 35 U.S.C. § 119 of Korean patent application number 10-2016-0129087 filed Oct. 6, 2016.

TECHNICAL FIELD

Embodiments of the present disclosure relate to a femoral tunnel guide device, and more particularly, to a femoral tunnel guide device for forming a femoral tunnel, which is used in anterior cruciate ligament reconstruction.

BACKGROUND ART

As sports activities and leisure activities have increased, the number of patients with injured cruciate ligaments continues to increase, and anterior cruciate ligament reconstruction for treating this is one of the operations widely used in the field of orthopedics.

Typical anterior cruciate ligament reconstruction is a method of reconstructing a new ligament at an isometric point instead of an anatomical position, and it is known that, although the success rate is about 80%, this method is unable to play a role in constraining rotation instability. Thus, to reconstruct a native anterior cruciate ligament (ACL), there has recently been an increasing interest in the concept of reconstructing an anterior cruciate ligament at an anatomical position (i.e., a position where an anterior cruciate ligament is attached to a bone in a normal human body).

DESCRIPTION OF EMBODIMENTS

Technical Problem

Provided is a femoral tunnel guide device capable of forming a femoral tunnel at an anatomical position using a method of passing through a tibial tunnel when anterior cruciate ligament reconstruction is performed.

Solution to Problem

According to an embodiment of the present disclosure, there is provided a femoral tunnel guide device including: a handle; a guide tube coupled to the handle and extending in one direction; and an offset unit extending from the guide tube and spaced apart by a predetermined distance from a virtual extension line of the guide tube in the one direction.

In the present embodiment, the predetermined distance may be in a range of 8 mm to 15 mm.

In the present embodiment, a guide pin having passed through the guide tube may be located at an anatomical position of an anterior cruciate ligament in a state in which the femoral tunnel guide device is inserted into a femur through a tibial tunnel.

In the present embodiment, the guide pin may be located at the anatomical position of an anterior cruciate ligament by rotation of the femoral tunnel guide device to a certain degree in a state in which the femoral tunnel guide device has passed through the tibial tunnel.

In the present embodiment, the offset unit may include: a connection portion extending from the guide tube; and a tongue portion extending from the connection portion and substantially parallel to the guide tube.

According to another embodiment of the present disclosure, there is provided a femoral tunnel guide device including: a handle; a guide tube coupled to the handle and extending in one direction; an offset unit provided at a first end portion of the guide tube, wherein a separation distance from a virtual extension line of the guide tube to the offset unit is adjustable in the one direction; and an offset controller connected to the offset unit and configured to control the separation distance between the offset unit and the guide tube.

In the present embodiment, the separation distance between the offset unit and the guide tube may be controlled to be in a range of 8 mm to 15 mm.

In the present embodiment, a guide pin having passed through the guide tube may be located at an anatomical position of an anterior cruciate ligament in a state in which the femoral tunnel guide device is inserted into a femur through a tibial tunnel.

In the present embodiment, the guide pin may be located at the anatomical position of an anterior cruciate ligament by rotation of the femoral tunnel guide device to a certain degree in a state in which the femoral tunnel guide device has passed through the tibial tunnel. In the present embodiment, the offset unit may include: a connection portion extending from the guide tube; a tongue portion base provided at a first end portion of the connection portion; a guide portion configured to be inserted into or withdrawn from the guide tube; and one or more links connecting the tongue portion base and the guide portion.

In the present embodiment, the connection portion, the guide portion, the one or more links, and the tongue portion base may form a four-section link.

In the present embodiment, the guide portion may be inserted into or withdrawn from the guide tube by controlling the offset controller, such that the separation distance between the guide tube and the offset unit is changed.

Additional aspects, features, and advantages other than those described above will become apparent from the accompanying drawings, the following claims, and the detailed description of the present disclosure.

Advantageous Effects of Disclosure

When a femoral tunnel guide device according to embodiments of the present invention is used, anatomical reconstruction of an anterior cruciate ligament using a transtibial method is facilitated, a short operating time is consumed as compared to other operations, surgical procedures are facilitated, and a tunnel is able to be formed at an anatomical position, and accordingly, patients may have good clinical results.

BEST MODE

Figure 1:
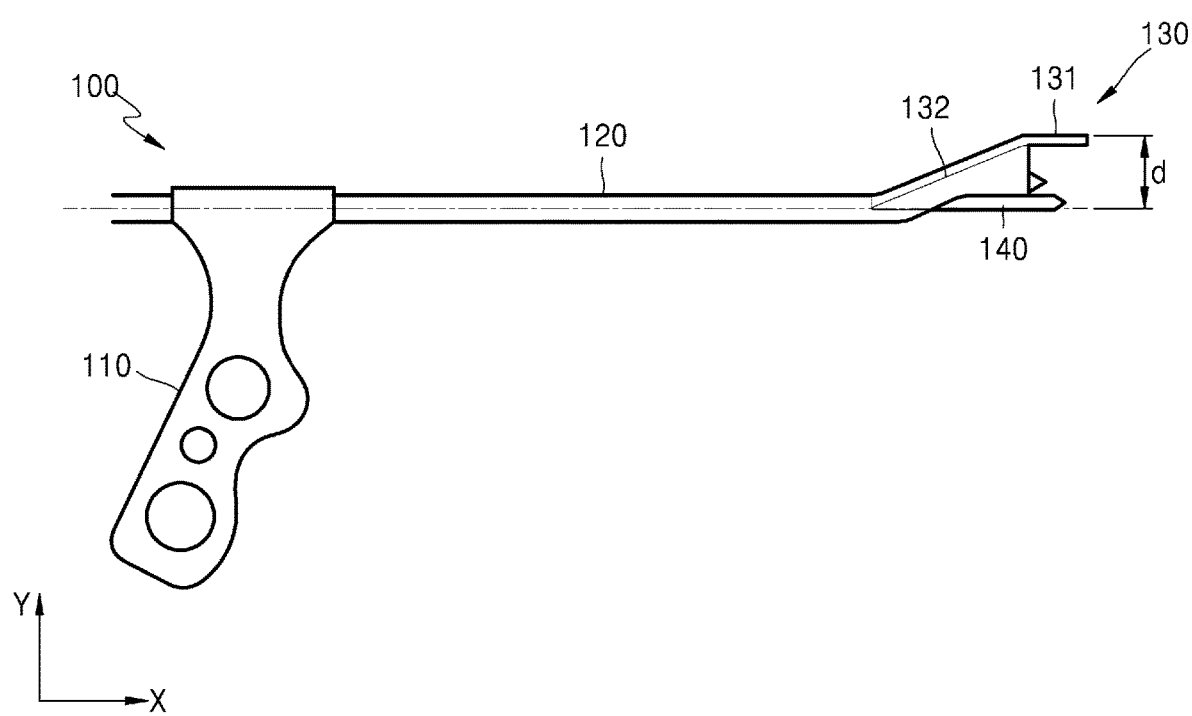
FIG. 1 is a side view of a femoral tunnel guide device according to an embodiment of the present disclosure.

As the present disclosure allows for various changes and numerous embodiments, particular embodiments will be illustrated in the drawings and described in detail. Effects, features, and methods of achieving these of the present disclosure will become apparent from the following detailed embodiments with reference to the accompanying drawings. However, the present disclosure is not limited to the embodiments set forth herein, and may be embodied in many different forms. In the embodiments described below, the terms first, second, and the like are not used for the purpose of limitation, but are only used to distinguish one element from another. In addition, an expression in the singular encompasses an expression in the plural unless it has a clearly different meaning in the context. In addition, the terms such as including, having, and the like are intended to indicate the existence of the features or components described in the specification, and are not intended to preclude the possibility that one or more other features or components may be added. In addition, in the drawings, the sizes of elements may be exaggerated or reduced for convenience of explanation. For example, the size and thickness of each element illustrated in the drawings are arbitrarily illustrated for convenience of explanation, and thus the present disclosure should not be limited to the illustrations of the drawings.

Hereinafter, embodiments of the present disclosure will be described in detail with reference to the accompanying drawings, like reference numerals denote like or corresponding components throughout the drawings, and a detailed description thereof will be provided once.

Figure 2:
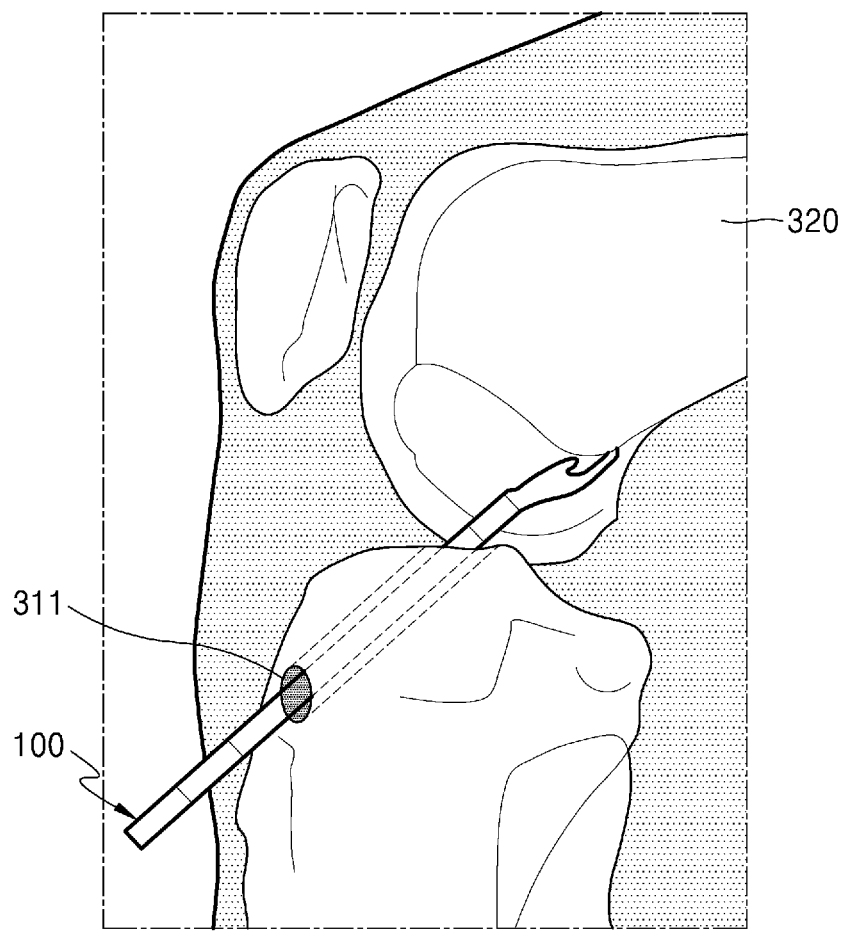
FIG. 2 is a conceptual view illustrating a process of performing anterior cruciate ligament reconstruction using the femoral tunnel guide device of FIG. 1.
Figure 3:
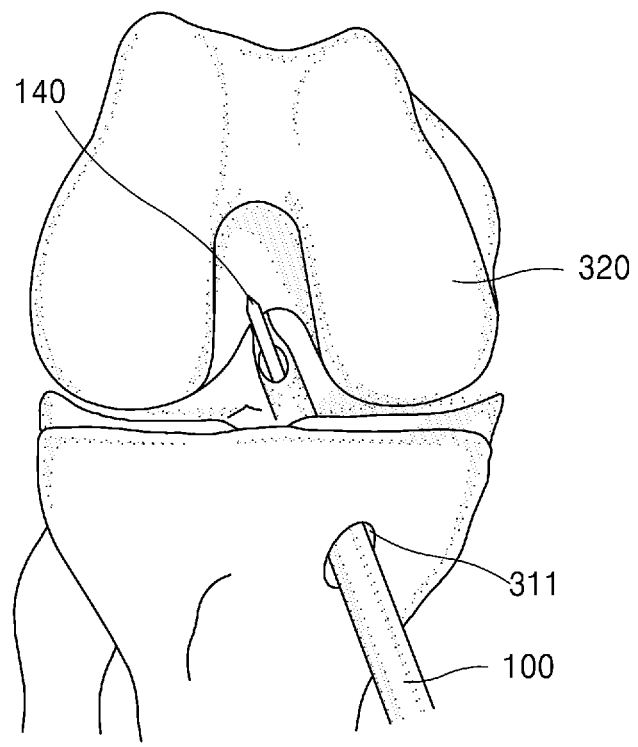
FIGS. 3 and 4 are views illustrating a process of locating a guide pin at an anatomical position by rotating the femoral tunnel guide device in the process of performing anterior cruciate ligament reconstruction using the femoral tunnel guide device of FIG. 1.
Figure 4:
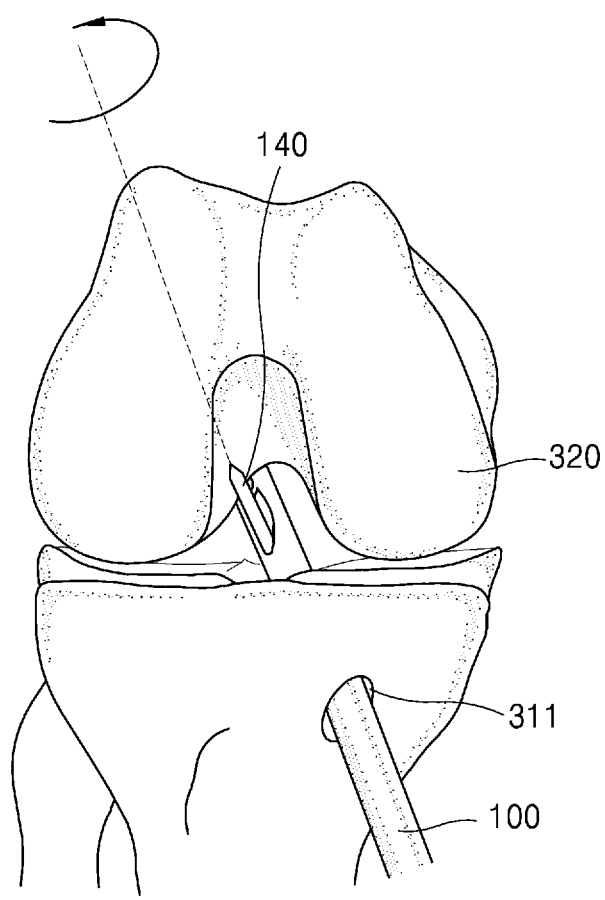

FIG. 1 is a side view of a femoral tunnel guide device 100 according to an embodiment of the present disclosure. FIG. 2 is a conceptual view illustrating a process of performing anterior cruciate ligament reconstruction using the femoral tunnel guide device 100 of FIG. 1. FIGS. 3 and 4 are views illustrating a process of locating a guide pin at an anatomical position by rotating the femoral tunnel guide device 100 in the process of performing cruciate ligament reconstruction using the femoral tunnel guide device 100 of FIG. 1.

First, referring to FIGS. 1 and 2, the femoral tunnel guide device 100 according to an embodiment of the present disclosure includes a handle 110, a guide tube 120, and an offset unit 130. This will be described in further detail as follows.

Recently, there has been an increasing interest in the concept of reconstructing an anterior cruciate ligament at an anatomical position to reconstruct a native anterior cruciate ligament (native AU), and various surgical methods have been introduced. That is, typical anterior cruciate ligament reconstruction is a method of reconstructing a new ligament at an isometric point instead of an anatomical position, but a tunnel is often placed anterosuperior to an anatomical position, and thus it is difficult to realize the anatomical position. In this case, it is known that, although the success rate is approximately 80%, this method is unable to play a role in constraining rotation instability.

Thus, many questions have been raised on the usefulness of a femoral tunnel guide device (i.e., a 7 mm fixed offset or the like) used by passing through a transtibial tunnel, which has been used in existing typical procedures. Recently, there has been an increasing interest in the concept of reconstructing an anterior cruciate ligament at an anatomical position to reconstruct a native anterior cruciate ligament (native AOL).

In the case of a tibial tunnel, consensus has been formed on surgical methods and instruments for forming a tunnel at an anatomical position. In the case of a femoral tunnel, however, various methods have been used to form a tunnel at an anatomical position, such as a method of using an additional anteromedial insertion hole, a double-incision outside-in method, a transtibial method, and the like. Among these, the method of using an additional anteromedial insertion hole is a method of forming a tunnel in a state in which a knee is excessively bent, but a poor field of vision is obtained and the posterior cortical bone is highly likely to be destroyed. Meanwhile, the double-incision outside-in method may enable the formation of a tunnel at an anatomical position without relatively excessive bending, but an additional incision is required in the femoral region. That is, the method of using an additional anteromedial insertion hole and the double-incision outside-in method are disadvantageous in that an operating method is not easy, and an additional incision and complications are highly likely to occur.

In addition, when a femoral tunnel is formed using the existing transtibial method, the femoral tunnel is often located at an anterosuperior position, thus causing a guide device to be internally rotated such that the guide device is able to reach an anatomical position, but even though a 7 mm offset femoral tunnel guide device, which is generally used, is internally rotated, a distance from the posterior femoral cortex to the guide device is restricted to 7 mm such that the femoral tunnel guide device is unable to reach the anatomical position.

To address the above-described problems, a femoral tunnel guide device according to an embodiment of the present disclosure is configured such that the device has an approximately 10 mm offset and facilitates the formation of a femoral tunnel at an anatomical position. Hereinafter, this will be described in more detail.

Referring back to FIGS. 1 and 2, the femoral tunnel guide device 100 includes the handle 110, the guide tube 120, and the offset unit 130.

The handle 110 may have various shapes and sizes such that a user is able to grasp the handle 110.

The guide tube 120 has a hollow tube shape, is provided on one side of the handle 110 and connected to the handle 110, and extends in one direction (an X-axis direction in the drawings). A first end portion of the guide tube 120 is connected to the handle 110, and the offset unit 130 is provided at a second end portion of the guide tube 120. As illustrated in FIG. 2, the guide tube 120 is thinner than a tibial tunnel such that the guide tube 120 is able to pass through and be inserted into the tibial tunnel, thus being rotatable in a state in which the guide tube 120 is penetratively inserted into the tibial tunnel. In addition, the guide tube 120 may enable a guide pin 140 to be inserted therethrough.

The offset unit 130 extends from the second end portion of the guide tube 120 and is spaced apart by a predetermined distance from a virtual extension line of the guide tube 120 in the one direction (i.e., the X-axis direction). In this regard, the offset unit 130 includes a connection portion 132 extending from the guide tube 120 and a tongue portion 131 provided at a first end portion of the connection portion 132. In this regard, the tongue portion 131 is substantially parallel to the guide tube 120 such that the tongue portion 131 is spaced apart from the virtual extension line of the guide tube 120 by a predetermined distance in the X-axis direction. This will be described in further detail as follows.

The femoral tunnel guide device 100 passes through a tibial tunnel 311 having been previously formed and determines the position of a femoral tunnel on the basis of a posterior cortical surface of a notch site of a femur 320. Specifically, when a femoral tunnel is formed using an existing transtibial method, the femoral tunnel is often located at an anterosuperior position, and thus efforts have been made to place a guide pin as close as possible to an anatomical position by using a method of internally rotating a femoral tunnel guide device. However, in the case of an existing femoral tunnel guide device, which has been used to form a femoral tunnel at an isometric point, a guide tube is spaced apart from an offset unit by a distance of 7 mm or less, and thus a problem, such as a short distance from the posterior cortical surface to the guide device even after the guide device is rotated, still occurs, and thus it is not easy for a guide pin to reach the anatomical position.

To address the above-described problems, in the femoral tunnel guide device 100 according to an embodiment of the present invention, the tongue portion 131 of the offset unit 130 is spaced apart from the virtual extension line of the guide tube 120 by a predetermined distance d, i.e., 8 mm to 15 mm, such that the guide pin 140 is located at the anatomical position of an anterior cruciate ligament in a state in which the femoral tunnel guide device 100 is inserted into the femur 320 through the tibial tunnel 311.

More particularly, as illustrated in FIG. 4, the guide pin 140 is located at the anatomical position of an anterior cruciate ligament by the femoral tunnel guide device 100 being rotated to a certain degree in an arrow direction, in a state in which the femoral tunnel guide device 100 passes through the tibial tunnel 311, as illustrated in FIG. 3.

In this regard, when considering a general case of the anatomical position of an anterior cruciate ligament, it is most preferable that the tongue portion 131 of the offset unit 130 is spaced apart from the virtual extension line of the guide tube 120 by a distance of approximately 10 mm.

When the femoral tunnel guide device according to embodiments of the present invention is used, the anatomical reconstruction of an anterior cruciate ligament using a transtibial method is facilitated, a short operation time is consumed as compared with other operations, surgical procedures are facilitated, and a tunnel is able to be formed at an anatomical position, and accordingly, patients may have good clinical results.

Mode of Disclosure

Hereinafter, a femoral tunnel guide device according to another embodiment of the present disclosure will be described.

Figure 5:
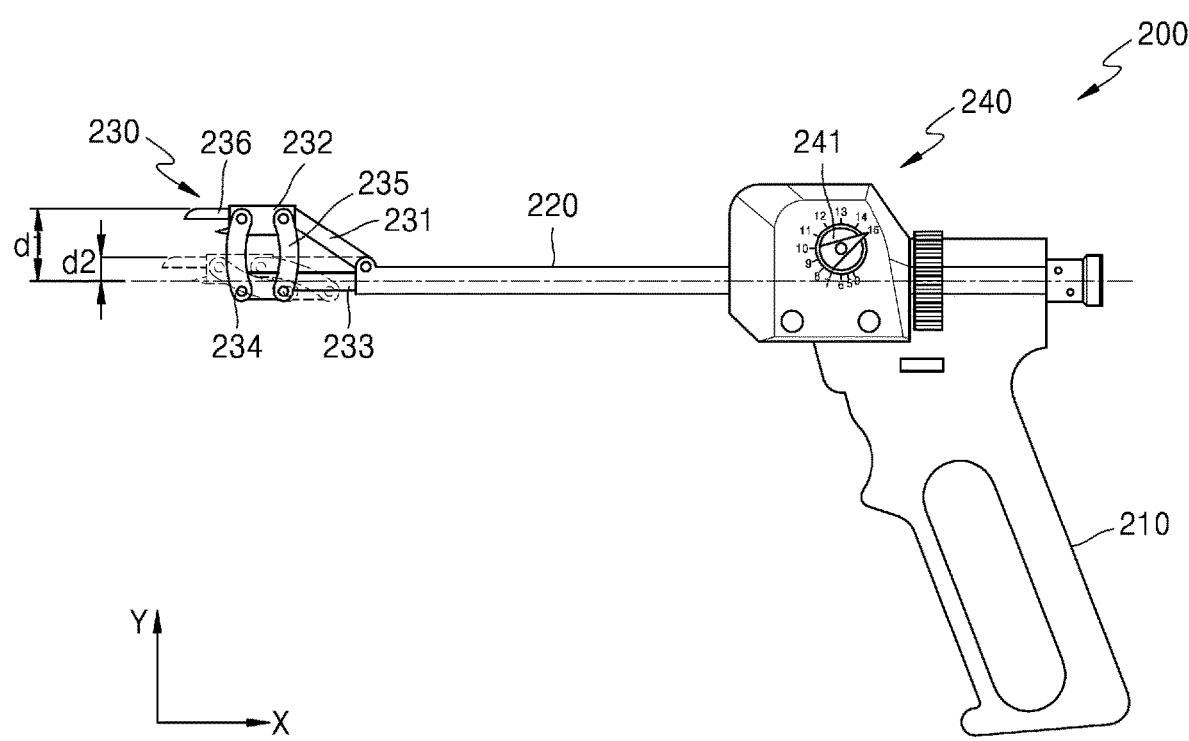
FIG. 5 is a side view of a femoral tunnel guide device according to another embodiment of the present disclosure.

FIG. 5 is a side view of a femoral tunnel guide device 200 according to another embodiment of the present disclosure.

Referring to FIG. 5, the femoral tunnel guide device 200 according to another embodiment of the present disclosure includes a handle 210, a guide tube 220, an offset unit 230, and an offset controller 240. This will be described in further detail as follows.

As described above, a femoral tunnel guide device according to an embodiment of the present disclosure is configured to form a femoral tunnel at an anatomical position. However, not all, patients have anterior cruciate ligament attachment sites at the same position, and a femoral tunnel guide device with various options has been required to more accurately form a femoral tunnel at an anatomical position, for each patient.

To this end, the femoral tunnel guide device 200 according to another embodiment of the present disclosure includes the offset unit 230, a separation distance of which from the guide tube 220 is adjustable, and the offset controller 240 configured to control the separation distance between the guide tube 220 and the offset unit 230, thereby providing an active offset femoral tunnel guide device in which an offset is controllable in a surgical field of vision so as to more accurately form a femoral tunnel at an anatomical position for each patient.

The handle 210 may have various shapes and sizes such that a user is able to grasp the handle 110.

The guide tube 220 has a hollow tube shape, is provided on one side of the handle 210 to be connected to the handle 210, and extends in one direction (an X-axis direction in the drawings). The handle 210 and the offset controller 240 are provided at a first end portion of the guide tube 220, and the offset unit 230 is provided at a second end portion of the guide tube 220. The offset unit 230 is thinner than a tibial tunnel such that the offset unit 230 is able to pass through and be inserted into the tibial tunnel, thus being rotatable in a state in which the offset unit 230 is penetratively inserted into the tibial tunnel.

The offset unit 230 extends from the second end portion of the guide tube 220 and is spaced apart by a predetermined distance from a virtual extension line of the guide tube 220 in the one direction (i.e., the X-axis direction). In this regard, the femoral tunnel guide device 200 according to another embodiment of the present disclosure is characterized in that a separation distance between the offset unit 230 and the guide tube 220 is adjustable.

To this end, the offset unit 230 includes a connection portion 231 extending from the guide tube 220, a tongue portion base 232 provided at a first end portion of the connection portion 231, and a tongue portion 236 provided on a first end portion of the tongue portion base 232. In this regard, the tongue portion base 232 and the tongue portion 236 are substantially parallel to the guide tube 220, and thus the tongue portion 236 is spaced apart from the virtual extension line of the guide tube 220 by a predetermined distance in the X-axis direction. Meanwhile, the offset unit 230 further includes a guide portion 233 inserted into or withdrawn from the guide tube 220, and one or more links, i.e., first and second links 234 and 235, connecting the tongue portion base 232 and the guide portion 233.

In addition, the offset controller 240 provided on one side of the guide tube 220 includes an offset selection unit 241, and by manipulation of the offset selection unit 241, the separation distance between the offset unit 230 and the guide tube 220 is adjusted while the guide portion 233 is inserted into or withdrawn from the guide tube 220. FIG. 5 illustrates that the offset selection unit 241 is in the form of a rotatable knob, and the guide portion 233 is inserted into or withdrawn from the guide tube 220 in accordance with rotation of the offset selection unit 241. That is, the offset selection unit 241 includes, on one side thereof, a power transmission member (not shown) configured to convert a rotation motion into a linear motion, such as a rack and pinion, or the like, and thus when the offset selection unit 241 is rotated, this may enable the guide portion 233 to be linearly moved such that the guide portion 233 is inserted into or withdrawn from the guide tube 220. However, the technical spirit of the present disclosure is not limited to the embodiments described above, and various components capable of converting the manipulation of the offset selection unit 241 into the linear movement of the guide portion 233 may be employed.

Meanwhile, the connection portion 231, the guide portion 233, the first link 234, and the tongue portion base 232 may form a four-section link. That is, when the guide portion 233 is withdrawn from the guide tube 220, a four-section link portion may be rotated clockwise overall such that the offset unit 230 and the guide tube 220 are separated from each other by a distance d1. In contrast, when the guide portion 233 is inserted into the guide tube 220, the four-section link portion may be rotated counterclockwise overall such that the offset unit 230 and the guide tube 220 are separated from each other by a distance d2.

In this regard, the separation distance between the offset unit 230 and the guide tube 220 is adjustable to be in a range of 8 mm to 15 mm, and thus a guide pin (not shown) having passed through the guide tube 220 is located at the anatomical position of an anterior cruciate ligament in a state in which the femoral tunnel guide device 200 is inserted into the femur 320 (see FIG. 2) through the tibial tunnel 311 (see FIG. 2).

When the femoral tunnel guide device according to embodiments of the present disclosure is used, anatomical reconstruction of an anterior cruciate ligament using a transtibial method is facilitated, and particularly, the separation distance between the offset unit 230 and the guide tube 220 is adjustable, thus enabling offset adjustment in a surgical field of vision such that a femoral tunnel can be more accurately formed at an anatomical position for each patient, thereby obtaining a significantly enhanced treatment effect.

While the present disclosure has been described with reference to embodiments illustrated in the drawings, these embodiments are provided for illustrative purposes only and it will be understood by those of ordinary skill in the art that various changes and modifications are made therein. Therefore, the true scope of the present disclosure should by defined by the technical spirit of the appended claims.

INDUSTRIAL APPLICABILITY

Embodiments of the present disclosure relate to a femoral tunnel guide device, and more particularly, to a femoral tunnel guide device for forming a femoral tunnel, which is used in anterior cruciate ligament reconstruction.

The invention claimed is:

1. A femoral tunnel guide device comprising:
a handle;
a guide tube coupled to the handle and extending in one direction;
an offset unit provided at a first end portion of the guide tube, wherein a separation distance from a virtual extension line of the guide tube to the offset unit is adjustable in the one direction; and
an offset controller connected to the offset unit and configured to control the separation distance between the offset unit and the guide tube,
wherein the offset unit comprises:
a connection portion extending from the guide tube;
a tongue portion base provided at a first end portion of the connection portion;
a guide portion configured to be inserted into or withdrawn from the guide tube; and
one or more links connecting the tongue portion base and the guide portion,
wherein the connection portion, the guide portion, the one or more links, and the tongue portion base form a four-section link,
wherein the connection portion is rotatably connected to the guide tube,
wherein a first end and a second end of the one or more links are rotatably connected to the tongue portion base and the guide portion, respectively,
wherein the guide portion is inserted into or withdrawn from the guide tube by controlling the offset controller, so that the connection portion and the one or more links rotate to change the separation distance between the guide tube and the offset unit.

2. The femoral tunnel guide device of claim 1, wherein the separation distance between the offset unit and the guide tube is controlled to be in a range of 8 mm to 15 mm.

3. The femoral tunnel guide device of claim 2, wherein a guide pin having passed through the guide tube is located at an anatomical position of an anterior cruciate ligament in a state in which the femoral tunnel guide device is inserted into a femur through a tibial tunnel.

4. The femoral tunnel guide device of claim 1, wherein a guide pin having passed through the guide tube is located at an anatomical position of an anterior cruciate ligament in a state in which the femoral tunnel guide device is inserted into a femur through a tibial tunnel.

5. The femoral tunnel guide device of claim 4, wherein the guide pin is located at the anatomical position of the anterior cruciate ligament by rotation of the femoral tunnel guide device in a state in which the femoral tunnel guide device has passed through the tibial tunnel.

* * * * *